United States Patent
Cox

(10) Patent No.: US 6,884,257 B1
(45) Date of Patent: Apr. 26, 2005

(54) STENT DELIVERY SYSTEM WITH ADJUSTABLE LENGTH BALLOON

(75) Inventor: Daniel L. Cox, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/727,019

(22) Filed: Nov. 28, 2000

(51) Int. Cl.[7] ............................................. A61F 2/06
(52) U.S. Cl. .................. 623/1.11; 604/103.05; 604/96; 606/192; 606/194
(58) Field of Search ................ 623/1.11; 606/108, 606/192, 194; 604/96

(56) References Cited

U.S. PATENT DOCUMENTS

| | | |
|---|---|---|
| 4,564,014 A | 1/1986 | Fogarty et al. |
| 4,649,922 A | 3/1987 | Wiktor |
| 5,226,889 A | 7/1993 | Sheiban |
| 5,246,421 A | 9/1993 | Saab |
| 5,514,093 A | 5/1996 | Ellis et al. |
| 5,522,882 A | 6/1996 | Gaterud et al. |
| 5,545,209 A * | 8/1996 | Roberts et al. ............ 623/1.11 |
| 5,549,551 A | 8/1996 | Peacock, III et al. |
| 5,628,755 A | 5/1997 | Heller et al. |
| 5,643,278 A | 7/1997 | Wijay |
| 5,645,560 A | 7/1997 | Crocker et al. |
| 5,676,654 A | 10/1997 | Ellis et al. |
| 5,725,535 A | 3/1998 | Hegde et al. |
| 5,843,092 A | 12/1998 | Heller et al. |
| 5,868,755 A * | 2/1999 | Kanner et al. ............ 606/108 |
| 5,891,154 A * | 4/1999 | Loeffler ................... 606/108 |
| 5,908,448 A * | 6/1999 | Roberts et al. ............ 623/1.23 |
| 5,961,536 A * | 10/1999 | Mickley et al. ........... 606/194 |
| 6,051,001 A * | 4/2000 | Borghi .................... 606/108 |
| 6,228,110 B1 * | 5/2001 | Munsinger ............... 623/1.12 |
| 6,447,540 B1 * | 9/2002 | Fontaine et al. .......... 623/1.12 |
| 2003/0144671 A1 * | 7/2003 | Brooks et al. ............ 606/108 |

* cited by examiner

Primary Examiner—David H. Willse
Assistant Examiner—Suzette J. Jackson
(74) Attorney, Agent, or Firm—Fulwider Patton Lee & Utecht LLP

(57) ABSTRACT

A stent delivery system with an adjustable length balloon. The system includes a stent delivery catheter having an expandable member with an inflated length that can be adjusted according to the length of a stent to be expanded. An exterior sheath having an expandable distal tip is disposed about the expandable member such that the sheath can be longitudinally adjusted so as to expose a desired length of the expandable member. The exposed length of the expandable member provides an effective working length required to expand the stent for deployment. Additionally, where subsequent expansions of the deployed stent may be necessary, post dilitation may be achieved by re-positioning the catheter and re-adjusting the sheath to form an effective working length of the expandable member which corresponds to the length of the stent that needs further expansion.

13 Claims, 6 Drawing Sheets

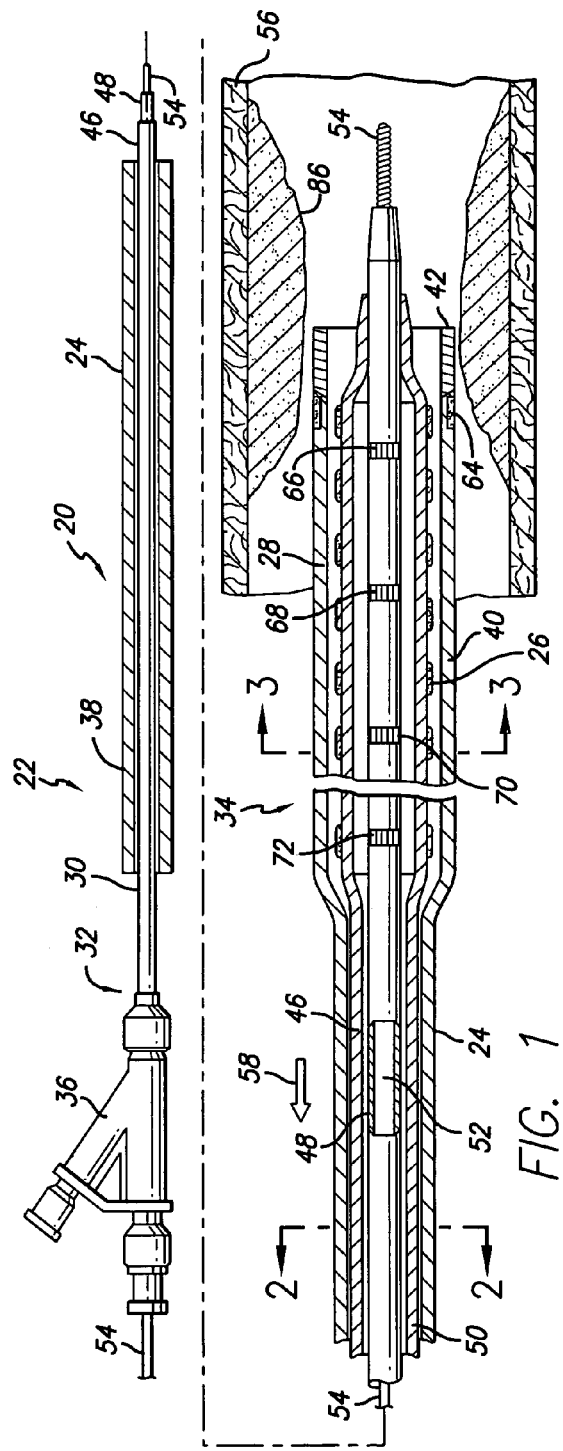
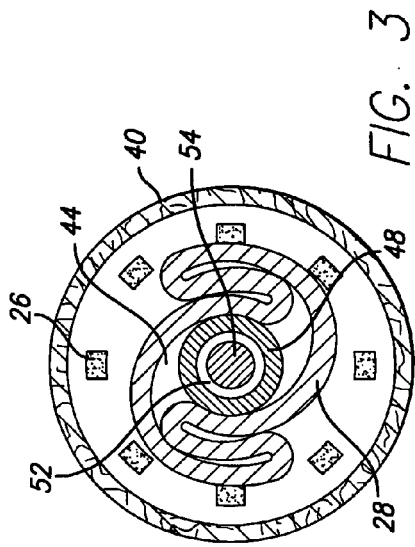
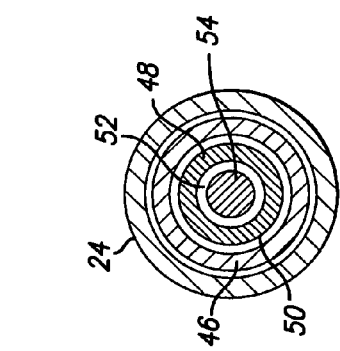

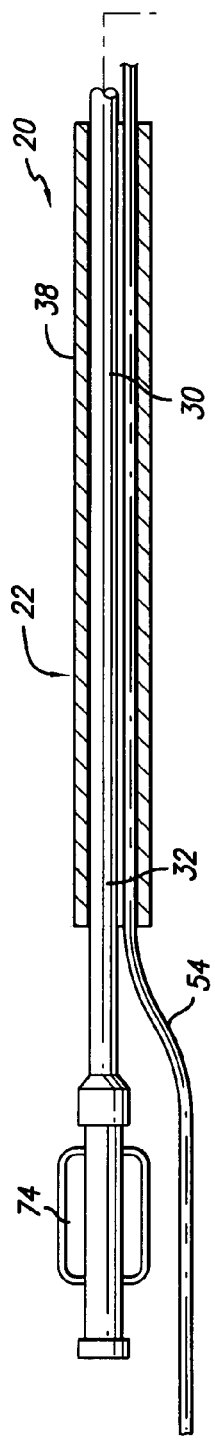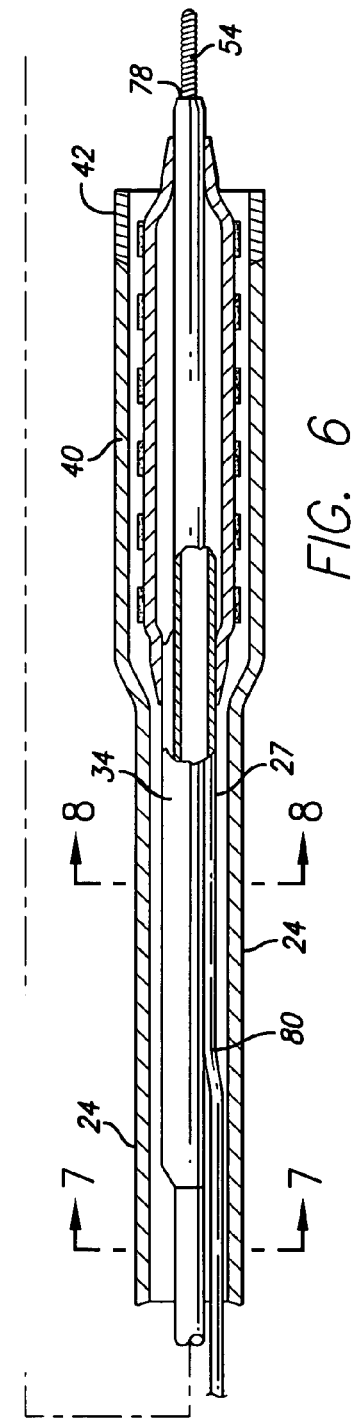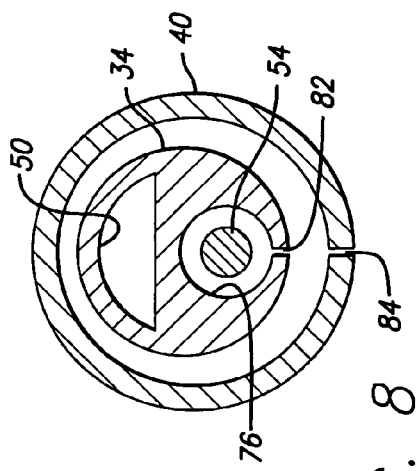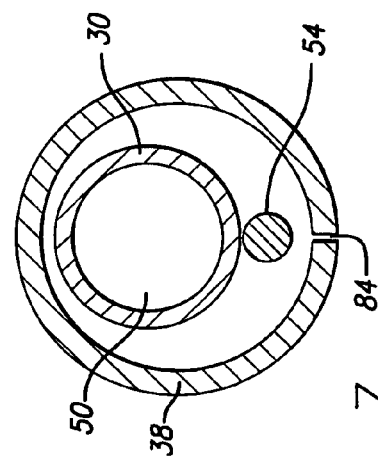

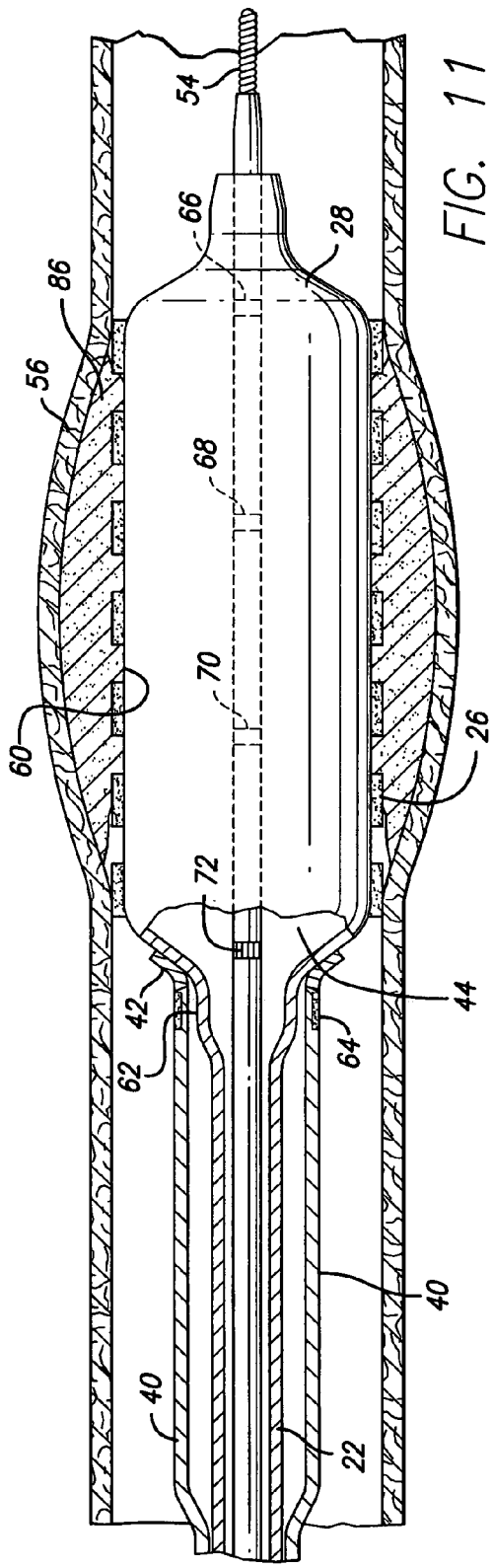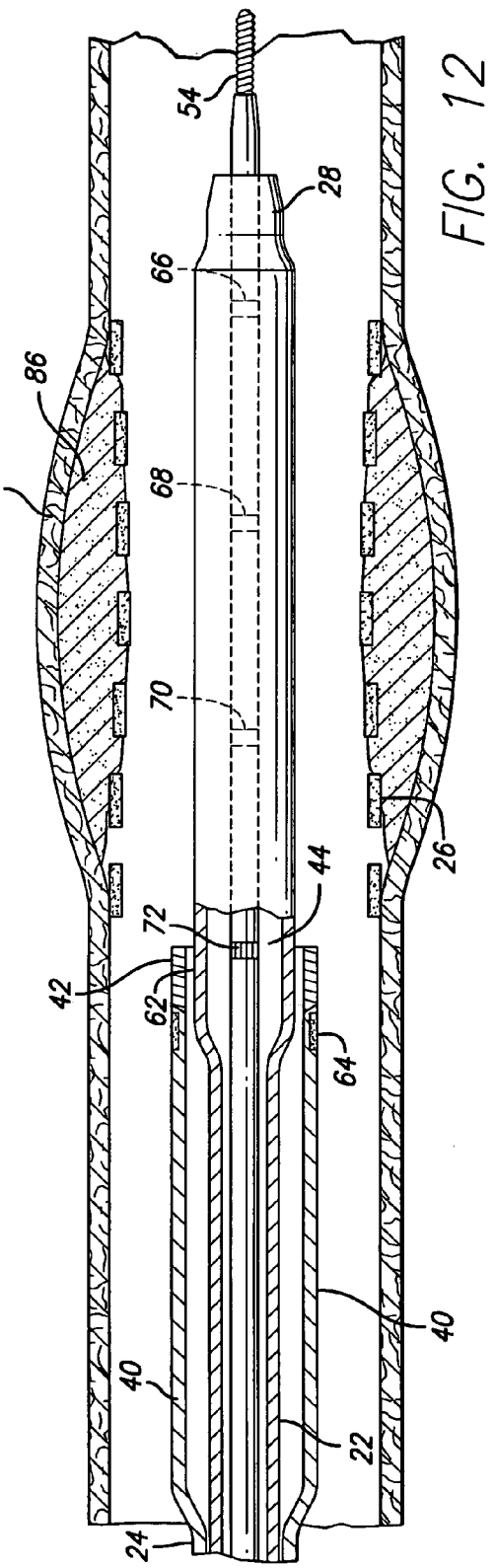

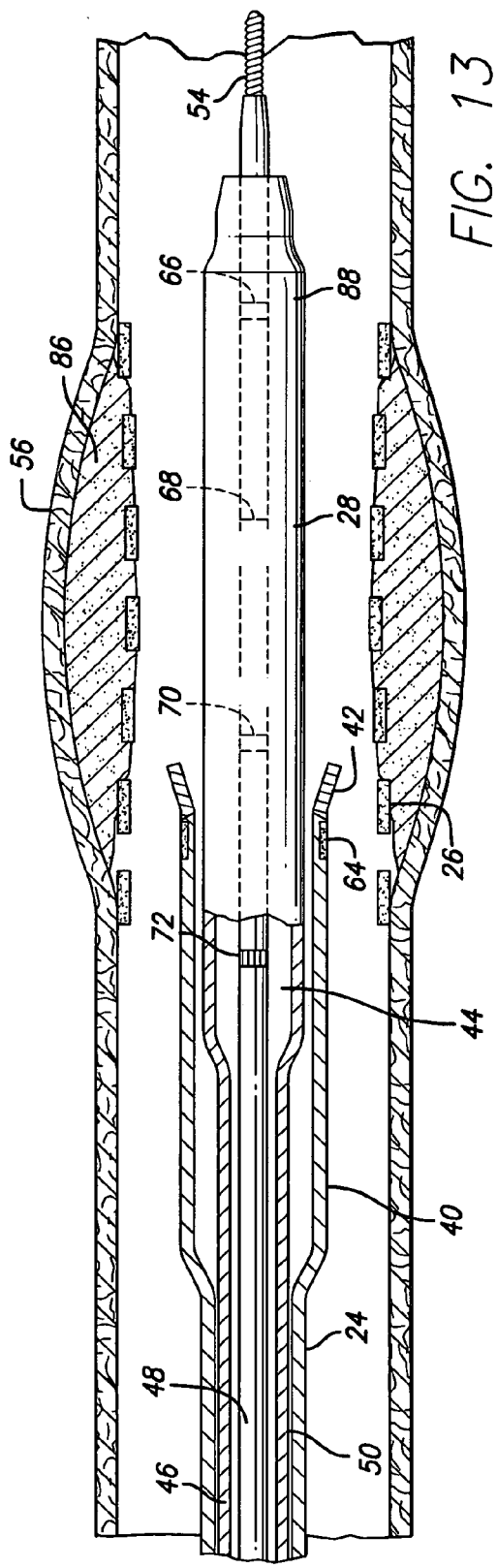
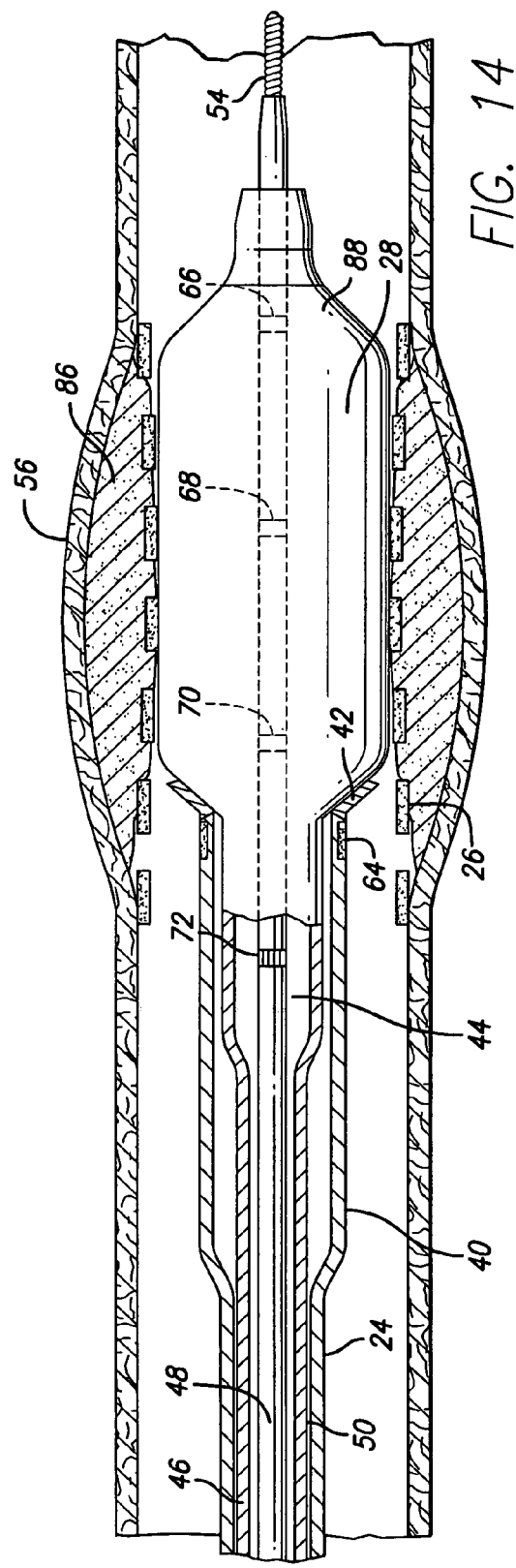

STENT DELIVERY SYSTEM WITH ADJUSTABLE LENGTH BALLOON

BACKGROUND OF THE INVENTION

This invention relates to devices for the treatment of heart disease and particularly to endo-arterial prosthesis, which are commonly called stents. More particularly, the invention relates to a stent delivery system having an adjustable length balloon catheter for interventional treatment of diseased vessels.

Several interventional treatment modalities are presently used for heart disease including balloon and laser angioplasty, atherectomy and by-pass surgery. In typical balloon angioplasty procedures, a guiding catheter having a performed distal tip is percutaneously introduced through the femoral artery into the cardiovascular system of a patient in a conventional Seldinger technique and advanced within the cardiovascular system until the distal tip of the guiding catheter is seated in the ostium. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon, which is made of relatively inelastic materials, is inflated to a predetermined size with radiopaque liquid at relatively high pressure (e.g., greater than four atmospheres) to compress the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom.

One problem which can occur during balloon angioplasty procedures is the formation of intimal flaps which can collapse and occlude the artery when the balloon is deflated at the end of the angioplasty procedure. Another problem characteristic of balloon angioplasty procedures is the large number of patients which are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

Much development work in the treatment of heart disease has been directed to stents. Stents are generally cylindrically shaped intravascular devices which are placed within an artery to hold it open. The device can be used to prevent restenosis and to maintain the patency of a blood vessel immediately after intravascular treatments. In some circumstances, they can also be used as the primary treatment device where they are expanded to dilate a stenosis and then left in place.

One prior art method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway thereof.

Generally, a stent requires an expandable member to be at least as long as the stent in order to fully expand the stent. Once the stent is deployed, it is sometimes necessary to post dilate certain areas of the stent at high pressure to more fully open the most constricted areas. If the expandable member is longer than the stent, the post dilation will also dilate unstented regions at the stent ends. This is undesirable as it can create edge dissections or increased restenosis. It is desirable to have the post dilation expandable member to be somewhat shorter than the delivery/deployment expandable member. One means of achieving this is to exchange the delivery system expandable member for a separate but shorter dilatation expandable member. However, this increases the procedure time and costs.

Some prior art stent delivery systems for implanting balloon expandable stents also utilize an outer delivery sheath which is initially placed over the compressed stent prior to deployment. A delivery sheath is sometimes needed to prevent the stent from moving axially along the balloon portion of the delivery catheter while being deployed into the patient's vasculature. Additionally, sometimes the stent cannot be deployed for a variety of reasons. In those instances, the stent must be able to be pulled back into the guiding catheter without being "stripped off" of the delivery catheter. Thus, the outer sheath remains in place over the compressed stent until the physician has manipulated the catheter into the proper location in the patient's vasculature. Thereafter, once in place, the physician can retract the outer sheath to expose the stent within the body vessel. The physician then can inflate the balloon portion of the dilatation catheter to cause the compressed stent to expand to a larger diameter to be left in place within the body vessel at the target site. Despite the care given during handling, stents can become dislodged from the delivery system. The consequences of losing a stent can range from embarrassment to a life-threatening situation that requires immediate surgery.

This outer delivery sheath also helps prevent the stent from abraiding the vessel wall as it is being delivered through the vasculature into the target area. Otherwise, the struts of the stent would be exposed to the vessel walls of the patient's vasculature and could possibly cause trauma to the walls or could cause pieces of plaque to break off from a stenosis as the delivery system is being positioned across a tight stenosis. Abrasive forces in the area of a stenosis are not desirable due to the possible formation of embolic debris which could be released into the patient's blood stream. Such debris could possibly occlude smaller blood vessels leading to vital organs, such as the brain.

What has been needed and heretofore unavailable is a stent delivery device, which allows for a variable length expandable member needed for proper stent deployment and safe and effective post dilation of a deployed stent. Also, the stent delivery device should be capable of increasing stent security by preventing the stent from moving axially along the balloon portion of the delivery catheter and should prevent the stent from abraiding the vessel wall as it is being delivered through the patient's vasculature. The present invention satisfies these and other needs.

SUMMARY OF THE INVENTION

The present invention is directed to a stent delivery system which provides an expandable member (balloon) with a variable working length to accommodate a wide variety of stent lengths. Additionally, the invention provides an efficient and cost-effective post-expansion dilation solution for instances where a deployed stent or the lesion in the patient's anatomy requires additional dilation.

The catheter assembly of the present invention has a catheter shaft with proximal and distal ends, an inner inflation lumen extending within the catheter shaft from the proximal end of the shaft to a location spaced proximally from the distal end of the shaft, an expandable member on the distal portion of the catheter shaft having an interior in fluid communication with the inner inflation lumen to facilitate inflation of the expandable member, and an adjustment member that provides control over the portion of the expandable member that expands upon the introduction of inflation fluid into the cavity of the expandable member. In some aspects, the expandable member may be an angioplasty dilitation balloon.

In one embodiment of the present invention, the adjustment member used to control the portion of expandable member that expands is an outer sheath with an inner lumen extending along the length thereof. The outer sheath includes a proximal section and a distal section, wherein the distal section is configured to envelop a stent mounted on an expandable member in a deflated condition. Because the distal section of the outer sheath is configured to envelop a stent mounted on the expandable member, the distal section may have a larger profile than the outer sheath proximal section. Preferably, the inner lumen of the distal section of the sheath has a larger internal diameter than the inner lumen of the proximal section of the sheath in order to facilitate receiving the expandable member in a deflated condition having a stent mounted thereon. The length of the distal section of the sheath that receives the expandable member should be at least one half of, but preferably as long as the length of the working surface of the expandable member. The sheath/dilitation catheter assembly is configured so that the sheath and the catheter are longitudinally moveable with respect to each other. The distal end of the sheath is provided with a greater degree of expandability so that when the expandable member is inflated the distal end of the sheath expands so as to shape the proximal taper of the expandable member. The sheath also is used to cover the collapsed stent to prevent it from moving axially along the expandable member of the dilatation catheter as the system is being deployed in the patient's vasculature. This sheath helps prevent the stent from being stripped off the delivery catheter or otherwise moved axially along the balloon length which can cause possible inaccurate placement during deployment. This sheath also acts as a protected covering which prevents the stent from abraiding the vessel wall as it is being delivered through the patient's vasculature.

The stent delivery catheter assembly of the present invention may be used essentially the same as a dilatation catheter. For example, when the aree of treatment is in the coronary artery, the assembly can be advanced through the patient's vasculature until its distal end is positioned within the ostium of the desired coronary artery. The sheath may be moved proximally with respect to the catheter to expose the desired length of the expandable member after the expandable member is positioned within the stenotic region to correspond to the desired length for a particular stent. For example, for the initial stent deployment, the working length of the expandable member may be chosen to be either slightly longer or the same size as the stent to be expanded. Thus, the current invention may be used as a generic stent delivery system for stents having different lengths.

Subsequent dilatations of the same stent may be required for areas of the stent which were not fully expanded upon the initial inflation of the expandable member. This post dilatation may require much higher pressure in a portion which was not completely expanded, because the stenosis at that portion was much harder than at other portions of the stent. Rather than subject the entire stent length to the higher pressure, the working length of the expandable member may be shortened (via the placement of the sheath over the expandable member) so that only the portion of the stent that had been incompletely expanded will be re-dilated. This avoids over-expansion and unnecessary injury in other areas of the stent or at the stent ends. Because there is an overall reduction of injury, and because pressure is focused only on the important areas, reduction of restenosis may be realized.

Additionally, the sheath supports the catheter and provides for improved pushability of the catheter, particularly with long expandable members, which have poor push transmission due to the long thin walled expandable member region of the distal shaft. An additional advantage of the sheath is that, after an initial dilation, the expandable member can be pulled back into the distal portion to re-groom the expandable member so that any wings, which may form when a vacuum is pulled on the interior of the expandable member, are wrapped about the inner tubular member extending through the interior of the expandable member rather than extend out laterally. This re-grooming reduces the effective profile of the deflated expandable member.

The stent delivery catheter of the invention provides a single catheter which can be used to expand stents having a wide range of lengths by merely adjusting the working length of the balloon. Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a longitudinal plan view, partially in section, of a stent delivery catheter assembly embodying features of the invention.

FIG. 2 is a transverse cross-sectional view of the catheter assembly shown in FIG. 1 taken along the lines 2—2.

FIG. 3 is a transverse cross-sectional view of the catheter assembly shown in FIG. 1 taken along the lines 3—3.

FIG. 6 is a longitudinal plan view, partially in section, of an alternative embodiment of the invention having a rapid exchange configuration.

FIG. 7 is a transverse cross-sectional view of the embodiment shown in FIG. 6 taken along the lines 7—7.

FIG. 8 is a transverse cross-sectional view of the embodiment shown in FIG. 6 taken along the lines 8—8.

FIG. 11 is a longitudinal plan view of a catheter distal section positioned at a diseased region of a vessel showing the expandable member in expanded form for initial expansion of a stent for treatment of the diseased region.

FIG. 12 is a longitudinal plan view of a catheter distal section wherein a stent has been initially expanded and the expandable member is in a deflated condition and the expanded stent is not uniformly expanded.

FIG. 13 is a longitudinal plan view of a catheter distal section wherein an expandable members working length is shortened, by adjusting the outer sheath proximally, to correspond with a required length for proper post expansion of the expanded stent.

FIG. 14 is a longitudinal plan view of a catheter distal section wherein an expandable member is inflated for a subsequent expansion operation on the initially expanded stent, the effective working length of the expandable member corresponds to the length of the stent that requires subsequent expansion.

DETAILED DESCRIPTION OF THE INVENTION

Figure 4:
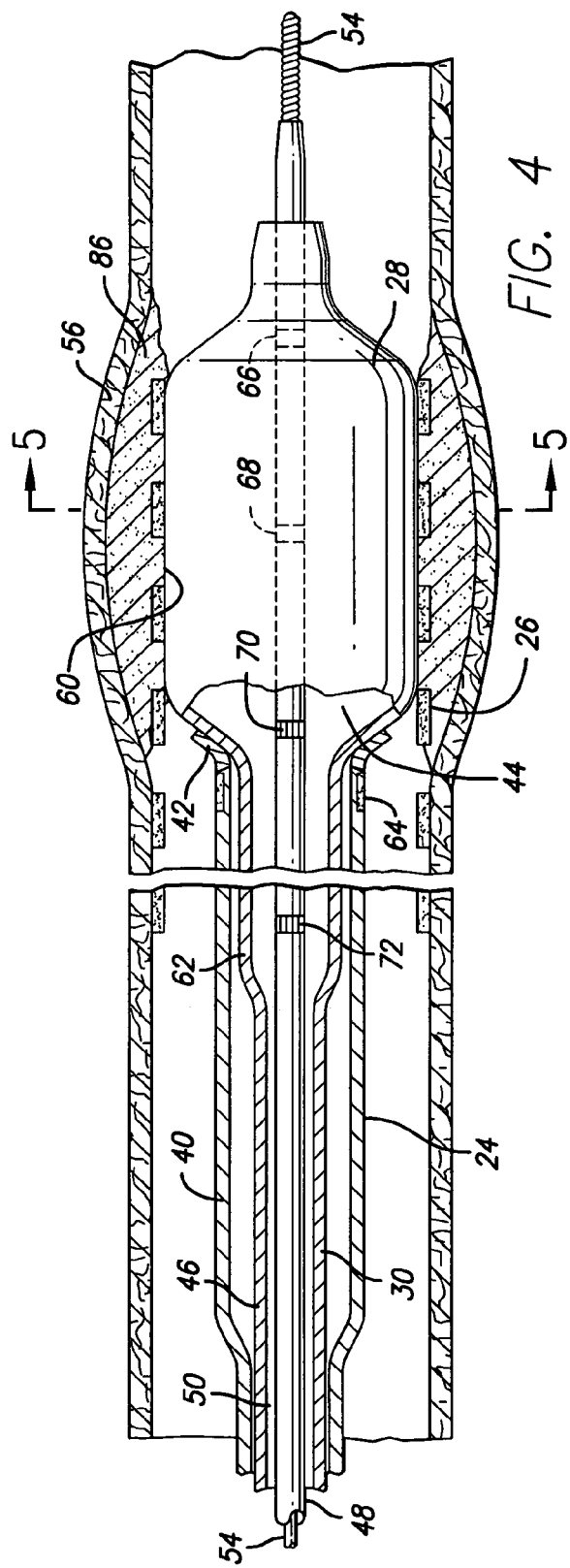
FIG. 4 is a partial longitudinal plan view of the assembly shown in FIG. 1 with the sheath partially removed from the expandable member and the exposed portion of the expandable member being inflated to post dilate a portion of a deployed stent.
Figure 5:
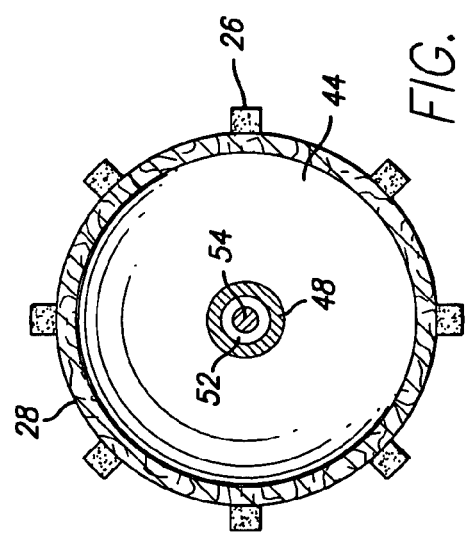
FIG. 5 is a transverse cross-sectional view of the catheter assembly shown in FIG. 4 taken along the lines 5—5.

Turning now to the drawings, in which like reference numerals represent like or corresponding elements in the drawings, FIGS. 1–5 illustrate a catheter assembly 20 embodying features of the invention. The catheter assembly includes a delivery catheter 22, an adjustment member (sheath) 24 and a stent 26. The delivery catheter includes an expandable member 28 (such as an inflatable dilatation balloon), an elongate catheter shaft 30 having a proximal end 32 and a distal end 34, and an adapter (sidearm) 36 mounted on the catheter shaft proximal end. The sheath includes a proximal section 38, a distal section 40 and a distal tip 42. The outer sheath is disposed about and is capable of sliding over the delivery catheter. The outer sheath distal portion is slightly expanded and is adapted to receive the expandable member. The expandable member has a cavity 44, and to maintain the expanded distal portion 40 of the sheath as small as possible, the cavity of the expandable member is preferably subjected to a vacuum to form as small a profile as possible, as shown in FIG. 3.

The catheter shaft 30 of the embodiment shown in FIGS. 1–5 is of a concentric design, configured with an outer tubular member 46 and an inner tubular member 48 disposed within the outer tubular member and defining with the outer tubular member an annular inflation lumen 50, which is configured to direct inflation fluid to the cavity 44 of the expandable member 28. The inner tubular member is provided with an inner lumen 52 which is configured to slidably receive a guide wire 54. If desired, the catheter shaft may be of dual lumen design such as depicted in the distal section of the embodiment shown in FIGS. 6–8 to be described hereinafter.

The sheath 24 is slidably disposed about the delivery catheter 22 so that when the catheter assembly 20 is advanced into the patient's artery 56 to expand a stent 26, the sheath can be moved proximally in relation to the delivery catheter, in the direction indicated by arrow 58 shown in FIG. 1. The sheath 24 is designed to cover at least a portion of the stent 26 as it is being delivered through the patient's vasculature. The sheath 24 helps prevent the stent from slidding axially on the expandable member 28 as it is being maneuvered into the treatment site. Additionally, the sheath serves as a protective barrier to help prevent the stent from abraiding the vessel walls of the body vessel as it is being manipulated into the target area. The sheath 24 also can be designed so that it covers the entire length of the stent 26 for delivery purposes. Referring now to FIG. 4, the sheath is moved in a proximal direction to partially uncover the expandable member 28, thereby defining an effective working length 60 (the uncovered portion) and a non-effective working length 62 (the covered portion), so that when inflation fluid is introduced into the cavity 44 of the expandable member, the effective working length (the uncovered portion) of the expandable member will expand to expand the stent. In this manner, the effective working length of the expandable member can be adjusted to accommodate stents of various lengths. The expanded distal section 40 of the sheath is sufficiently inelastic to retain the non-effective working length (the uncovered portion) of the expandable member within the sheath distal section and to prevent the significant inflation thereof. Upon the completion of the expansion, the expandable member may be deflated and pulled completely back into the expanded distal portion of the sheath so that both the balloon catheter and the sheath of the catheter assembly can be removed together.

As shown in FIGS. 1 and 4, the sheath 24 may have an elastically expandable distal tip 42 which conforms to and, to a certain extent, shapes the proximal end of the inflated portion of expandable member 28. When the expandable member is deflated, the expanded distal tip will elastically recoil to essentially its pre-expanded size. A radiopaque marker 64 may be provided on the sheath distal section 40 at a location just proximal to the expandable distal tip. The radiopaque marker allows the physician to determine fluoroscopically the location of the proximal end of the sheath within a patient's vasculature. One or more radiopaque markers 66, 68, 70 and 72 are provided on the inner tubular member 48 within the expandable member 28 to allow the physician to determine the relative position of the distal end of the sheath with respect to the expandable member, i.e., how much of the expandable member extends out of the sheath. The expandable distal tip 42 may have radiopaque material incorporated therein, e.g. barium salt, in lieu of the radiopaque marker 64.

The working length of the expandable member 28 is generally at least about two centimeters (cm), preferably about four to about twenty cm. The inflated diameter of the expandable member may range from about 0.5 to about ten millimeters (mm), preferably from about one to about four mm.

The catheter shaft 30, the expandable member 28 and the sheath 24 can be formed from conventional materials such as melt processable thermoplastic polymers, e.g. polyethylene, polyethylene terephthalate, polyester-polyamide such as HYTREL and an ionomer such as SURLYN, which are available from the E. I. DuPont, deNemours & Company. The sheath can be formed in a multi-layered laminate construction, e.g. where one layer of the laminate may be a relatively high strength to withstand the expandable member inflation pressure without significant expanding (e.g. polyethylene terephthalate or a high density polyethylene) and the another layer may be a relatively low strength but more flexible to provide good flexibility for tracking (e.g. a polyester-polyamide such as HYTREL, a low density polyethylene or a suitable polyurethane.) Braided or wound supporting strand may be incorporated into the wall of the sheath to provide, in whole or in part, resistance to expansion while maintaining flexibility. A lubricious coating can be utilized on the inner surface of the sheath to reduce or limit the frictional force created between the sheath and the collapsed stent. For example, a hydrophilic coating on the inner surface of the sheath can reduce frictional forces. Additionally, the inner surface of the sheath can be lined with a material such as polytetrafluoroethylene (PTFE) which will decrease the frictional forces generated between sheath and stent. Coatings such as Microglide® which is well-known in the art, along with other suitable lubricious coating can be used.

Reference is made to FIGS. 6–8, which depict an embodiment of the invention with rapid exchange features. The catheter assembly 20 includes a rapid exchange type delivery catheter 22 and an outer sheath 24. The delivery catheter includes a catheter shaft 30, an expandable member 28 and an a sidearm 74. The sheath includes a proximal section 38 and an expanded distal section 40, which is configured to receive a deflated expandable member. The sheath is provided with an expandable distal tip 42, as in the prior embodiment. The catheter shaft includes a proximal section 32 and a distal section 34. The catheter shaft proximal section is configured in a single lumen design, and includes only an inflation lumen 50. The catheter shaft distal section is of dual lumen design and includes the inflation lumen extending from the shaft proximal section and a guide wire lumen 76 that extends between a distal guide wire port 78 in the distal end of the catheter and a proximal guide wire port 80, which is located proximal to the expandable member and spaced a distance (e.g., about five to about fifty cm) from the distal end of the catheter. A guide wire 54 may be disposed within the guide wire lumen.

A slit 82 may be provided in the catheter shaft distal section 34 to facilitate removal of the guide wire 54 therefrom. A slot 84 may also be provided in the sheath proximal section 38 for the same reason and to allow longitudinal movement of the sheath 24 relative to the rapid exchange delivery catheter.

The shaft distal section 34 may be formed of melt processable thermoplastic polymer material such as polyethylene or a polyester-polyamide such as HYTREL. If desired, the sheath proximal section 38 may be provided with a proximal guide wire port (not shown) to facilitate the rapid exchange of the sheath at a location proximal to the proximal guide wire port 80. The shaft proximal section 32 may also be provided with a longitudinal groove (not shown) on the same side of the shaft as the proximal guide wire port 80. The longitudinal groove is configured to receive a guide wire extending out of the proximal guide wire port to reduce the profile of the entire assembly proximal to the proximal guide wire port.

Referring to FIG. 9–14, in keeping with one method of use for the current invention, an adjustable length balloon catheter assembly 20 having a proximal section and a distal section is provided. The catheter assembly includes a balloon catheter 22, an outer sheath 24 and a stent 26. The balloon catheter includes an elongated catheter shaft 30 having a proximal section 32, a distal section 34, and a sidearm 36 mounted on the proximal end of the catheter shaft's proximal section. Additionally, an expandable member 28 is positioned at a location on the catheter shaft distal section. The outer sheath includes an a proximal section 38 and a distal section 40. The outer sheath is disposed about and is capable of sliding over the balloon catheter. The outer sheath distal portion is slightly expanded and is adapted to receive the expandable member in its deflated condition.

A stent 26 may be mounted onto the expandable member 28 of the catheter distal section 34 and may be enclosed by the sheath 24 for delivery into a diseased vessel 56. A guide wire 54 is advanced into the vessel until it is positioned at a diseased target site 86 with the proximal end of the guide wire remaining outside the patient. The catheter assembly 20 is then advanced over the guide wire until the distal end of the catheter shaft 30 is positioned at a location just proximal to the diseased target site. Up to this point, the stent is enclosed and protected by the sheath of the catheter assembly during the advancement and positioning of the catheter distal section.

Figure 9:
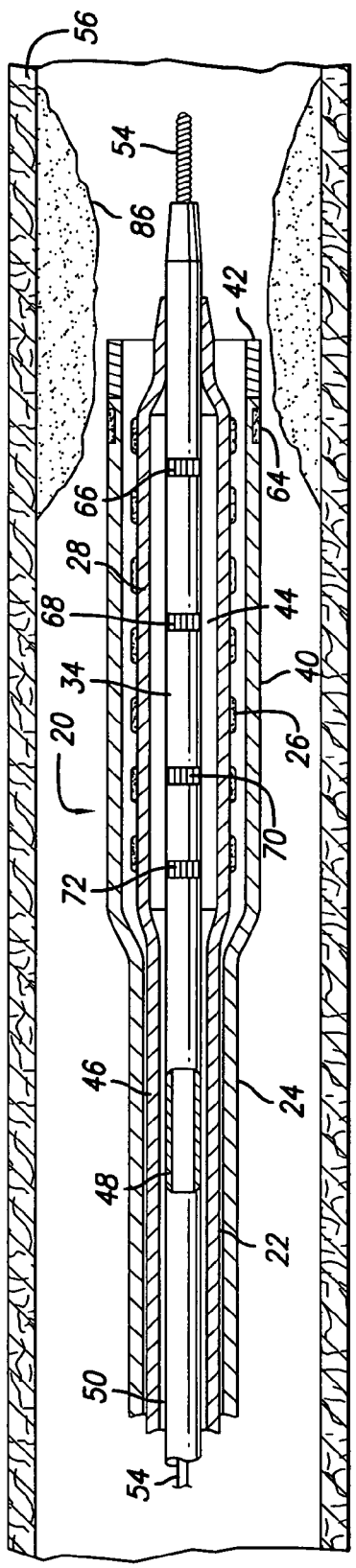
FIG. 9 is a longitudinal plan view of a catheter distal section as it is delivered over a guide wire toward a diseased region of a vessel for treatment by the placement of a stent.
Figure 10:
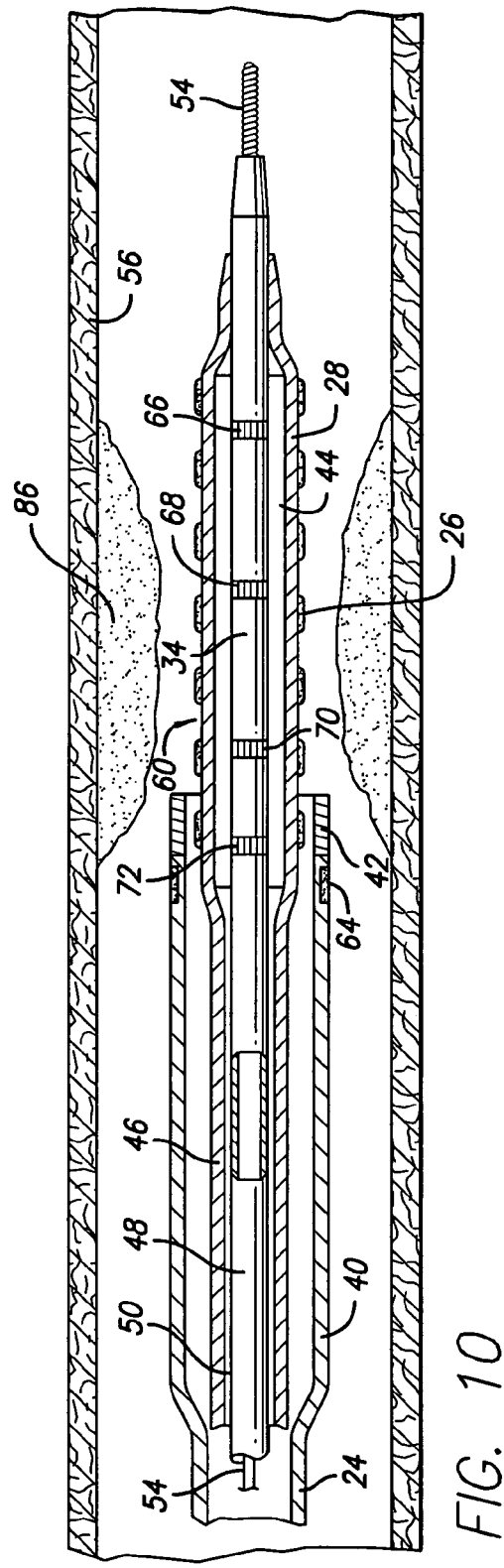
FIG. 10 is a longitudinal plan view of a catheter distal section positioned at a diseased region of a vessel showing an outer sheath retracted to allow for an expandable member to have an effective working length that corresponds to the length of a stent to be expanded.

As shown in FIG. 9, the catheter assembly 20 is advanced to a diseased site, once the catheter distal section 34 has been advanced to the diseased site 86, the sheath 24 may be retracted to expose the stent 26 mounted the expandable member 28. Retraction of the sheath is accomplished by the physician pulling the sheath proximal end 38 proximally with respect to the delivery catheter 22 (FIG. 10). Proper retraction of the sheath allows the expandable member to be exposed, thereby forming an effective working length 60.

Under fluoroscopic examination, various effective working lengths may be realized by the alignment of a radiopaque marker 64 on the distal end of the sheath distal section 40 with any one of various locations marked by one or more radiopaque markers 66, 68, 70 and 72 located at various positions along the catheter shaft distal section 34 within the expandable member 24. For initial deployment of the stent 26, the required effective working length 60 may be the length of the stent. Under fluoroscopic examination, the operation may be visualized and the sheath may be retracted to a position where radiopaque marker 64 on the sheath distal section 40 may be aligned with the most proximally located radiopaque marker 72 of the catheter shaft distal section 34. The alignment of the sheath radiopaque marker with radiopaque marker 72 provides a desired effective working length 60 of the expandable member that corresponds with the proximal end of the stent, thereby providing full coverage of the entire stent length (FIG. 10).

As shown in FIG. 11, the effective working length 60 of the expandable member 28 is inflated when inflation fluid is introduced into the cavity 44 of the expandable member. The effective working length of the expandable member will expand to initially expand and deploy the stent 26. Once the stent is deployed, the expandable member may be deflated and re-groomed into the sheath 24 (FIG. 12). Often times, the deployed stent may not have expanded evenly due to various factors such as stent material stiffness or the hardness of the diseased area; therefore, subsequent expansion of various areas of the stent may be required to touch up the stent. As shown in FIG. 13, the catheter assembly 20 may be re-positioned within the diseased vessel 56 to perform subsequent expansion of the deployed stent where desired. To perform a subsequent expansion operation, the catheter assembly may be re-positioned such that the expandable member distal end 88 is aligned with the distal portion of the stent that requires further expansion. The effective working length of the expansion member may then be adjusted by moving the sheath proximally or distally in relation to the balloon catheter to allow for a shorter effective working length.

As shown in FIG. 13, a subsequent effective working length 60 may be selected that will correspond to the length of the stent 26 that needs further expansion. The sheath 24 may be adjusted distally such that the radiopaque marker 64 on the sheath distal end is aligned with a radiopaque marker 70 that is located distal to radiopaque 22 of the catheter shaft distal section 34, thereby creating a shorter effective working length that corresponds with the length of the stent needing further expansion. As shown in FIG. 14, once the desired effective working length of the expandable member 28 is achieved, inflation fluid is introduced into the cavity 44 of the expandable member. The shorter effective working length of the expandable member will expand to further expand the stent. Still further subsequent expansions may be necessary, in which case, the steps of re-positioning the catheter assembly 20 and re-adjusting the expandable member effective working length may be repeated.

From the foregoing, it will be appreciated that the stent delivery assembly 20 of the invention provides an adjustable length expandable member 28 for proper expansion and deployment of stents 26 having different lengths. When necessary, subsequent expansion operations (post-dilation) may be quickly and precisely performed on a deployed stent where there are areas of the deployed stent that may have been unevenly expanded. The present invention provides a single catheter assembly for multiple operations. Furthermore, the assembly increases safety while reducing the cost and complexity of intravascular procedures by negating the necessity of using multiple catheters having different expandable member lengths.

The invention has been described herein in terms of stent delivery assembly. It will be readily apparent to those skilled in the art that various modifications and improvements may be made to the invention. For example, elements of one embodiment may be used with another embodiment, such as the concentric shaft design shown in FIGS. 6–8 may be used in the embodiment shown in FIGS. 1–5 in lieu of the dual lumen design. While several particular forms of the invention have been illustrated and described, it will be apparent that various modifications can be made without departing from the spirit and scope of the invention. Accordingly, it is not intended that the invention be limited, except as by the appended claims.

What is claimed is:

1. A stent delivery catheter assembly, comprising:
   a catheter including an elongated catheter shaft having a proximal end and a distal end with an inner inflation lumen extending therein;
   an expandable member having a proximal end and a distal end, a length and a desired inflated diameter disposed near the distal end of the elongated catheter shaft which is in fluid communication with the inner inflation lumen, the expandable member being adapted to receive a stent for mounting thereon;
   a stent mounted on the expandable member; and
   a moveable sheath adapted to cover a portion of the stent during delivery and having an inner lumen with smaller diameter than the desired inflated diameter of the expandable member, the sheath being movable over a portion of the expandable member so that only a portion of the expandable member not covered by the sheath expands to the desired inflated diameter upon inflation to create a working length of the expandable member which is at least as long as the length of the stent mounted on the expandable member, the sheath possessing sufficient strength to prevent any portion of the expandable member covered by the sheath from expanding when the expandable member is inflated, wherein the sheath has a proximal and a distal portion and the inner lumen which extends within the distal portion of the sheath is provided with larger internal transverse dimensions than the inner lumen of the proximal portion thereof to facilitate receiving the stent and the expandable member.

2. The stent delivery catheter assembly of claim 1, wherein:
   the stent has a length which is smaller than the length of the expandable member.

3. The stent delivery catheter assembly of claim 1, wherein:
   the moveable sheath covers the entire stent during delivery.

4. The stent delivery catheter assembly of claim 1, wherein:
   the moveable sheath includes an inner surface having a lubricious coating decrease friction between the sheath and stent.

5. A stent delivery catheter assembly, comprising:
   a catheter including an elongated catheter shaft having a proximal end and a distal end with an inner inflation lumen extending therein;
   an expandable member having a proximal end and a distal end, a length and a desired inflated diameter disposed near the distal end of the elongated catheter shaft which is in fluid communication with the inner inflation lumen, the expandable member being adapted to receive a stent for mounting thereon;
   a moveable sheath adapted to cover a portion of the stent during delivery and having an inner lumen with smaller diameter than the desired inflated diameter of the expandable member, the sheath being movable over a portion of the expandable member so that only a portion of the expandable member not covered by the sheath expands to a desired inflated diameter upon inflation; and
   a stent mounted on the expandable member, wherein:
      the moveable sheath has a distal tip which is substantially expandable and expands as the expandable member is expanded.

6. A method of delivering a stent within an area of treatment in a body lumen, comprising:
   mounting a stent upon an expandable member having a length greater than the length of the stent;
   covering the stent and expandable member with a moveable sheath which is disposed in a co-axial arrangement over the stent and expandable member, the sheath possessing sufficient strength to prevent any portion of the expandable member covered by the sheath from expanding when the expandable member is inflated;
   advancing the stent and expandable member into the area of treatment in the body vessel;
   retracting the sheath to expose the mounted stent on the expandable member, the moveable sheath being placed along the expandable member to create a working length of the expandable member in which only the portion of the expandable member not covered by the sheath will expand when inflated;
   inflating the expandable member to create the working length which is at least as long as the stent to expand the stent within the body vessel; and
   deflating the expandable member, wherein:
      after the expandable member has been deflated, the sheath is moved over the expandable member to create a working length of the expandable member which is utilized to expand any portion of the stent which has not been fully deployed within the area of treatment.

7. The method of claim 6, further comprising:
adjusting the position of the expandable member within the area of treatment to perform subsequent expansion of the initially expanded stent.

8. The method of claim 6, wherein:
when the sheath is retracted to expand from the stent, an effective working length is created on the expandable member which corresponds to the length of the stent.

9. A catheter assembly for delivering and deploying an implantable medical device in a patient, comprising:
a catheter including an elongated catheter shaft having a proximal end and a distal end with an inner inflation lumen extending therein;
an expandable member having a proximal end and a distal end, a length and a desired inflated diameter disposed near the distal end of the elongated catheter shaft which is in fluid communication with the inner inflation lumen, the expandable member being adapted to receive a medical device for mounting thereon;
a medical device mounted on the expandable member; and
a moveable sheath having an inner diameter large enough to allow the sheath to cover the medical device during delivery, the inner diameter of the sheath being smaller than the desired inflated diameter of the expandable member, the sheath being movable to cover a portion of the expandable member and possessing sufficient strength to prevent the covered portion of the expandable member from expanding when the expandable member is inflated, wherein the moveable sheath has a distal tip which is substantially expandable and expands as the expandable member is expanded.

10. A stent delivery catheter assembly, comprising:
a catheter including an elongated catheter shaft having a proximal end and a distal end with an inner inflation lumen extending therein;
an expandable member having a proximal end and a distal end, a length and a desired inflated diameter disposed near the distal end of the elongated catheter shaft which is in fluid communication with the inner inflation lumen, the expandable member being adapted to receive a stent for mounting thereon;
a stent mounted on the expandable member; and
a moveable sheath adapted to cover a portion of the stent during delivery and having an inner lumen with smaller diameter than the desired inflated diameter of the expandable member, the sheath being movable over a portion of the expandable member so that only a portion of the expandable member not covered by the sheath expands to the desired inflated diameter upon inflation to create a working length of the expandable member which is at least as long as the length of the stent mounted on the expandable member and wherein the sheath has a proximal and a distal portion and the inner lumen that extends within the distal portion of the sheath is provided with larger internal transverse dimensions than the inner lumen of the proximal portion thereof to facilitate receiving the stent and the expandable member.

11. A method of delivering a stent within an area of treatment in a body lumen, comprising:
mounting a stent upon an expandable member having a length greater than the length of the stent;
covering the stent and expandable member with a moveable sheath which is disposed in a co-axial arrangement over the stent and expandable member;
advancing the stent and expandable member into the area of treatment in the body vessel;
retracting the sheath to expose the mounted stent on the expandable member, the moveable sheath being placed along the expandable member to create a working length of the expandable member in which only the portion of the expandable member not covered by the sheath will expand when inflated;
inflating the expandable member to create the working length which is at least as long as the stent to expand the stent within the body vessel;
deflating the expandable member; and
moving the sheath over the expandable member to create a working length of the expandable member which is utilized to expand any portion of the stent which has not been fully deployed within the area of treatment.

12. The method of claim 11, further comprising:
adjusting the position of the expandable member within the area of treatment to perform subsequent expansion of the initially expanded stent.

13. The method of claim 11, wherein:
when the sheath is retracted to expand from the stent, an effective working length is created on the expandable member which corresponds to the length of the stent.

* * * * *